(12) United States Patent
Le et al.

(10) Patent No.: US 10,799,140 B2
(45) Date of Patent: Oct. 13, 2020

(54) SYSTEM AND METHOD FOR INSTRUCTING A BEHAVIOR CHANGE IN A USER

(71) Applicant: Emotiv, Inc., San Francisco, CA (US)

(72) Inventors: Tan Le, San Francisco, CA (US); Geoffrey Mackellar, San Francisco, CA (US)

(73) Assignee: Emotiv Inc., San Francisco, CA (US)

( * ) Notice: Subject to any disclaimer, the term of this patent is extended or adjusted under 35 U.S.C. 154(b) by 545 days.

(21) Appl. No.: 15/683,581

(22) Filed: Aug. 22, 2017

(65) Prior Publication Data

US 2017/0347907 A1 Dec. 7, 2017

Related U.S. Application Data

(63) Continuation of application No. 13/903,832, filed on May 28, 2013, now Pat. No. 9,763,592.
(Continued)

(51) Int. Cl.
*A61B 5/04* (2006.01)
*A61B 5/0482* (2006.01)
(Continued)

(52) U.S. Cl.
CPC ............ *A61B 5/0482* (2013.01); *A61B 5/486* (2013.01); *G06F 19/3481* (2013.01);
(Continued)

(58) Field of Classification Search
None
See application file for complete search history.

(56) References Cited

U.S. PATENT DOCUMENTS 4,421,122 A 12/1983 Duffy
6,230,049 B1 5/2001 Fischell et al.
(Continued)

FOREIGN PATENT DOCUMENTS

WO 147913 12/2010

OTHER PUBLICATIONS

Park, et al. "Multiscale Entropy Analysis of EEG from Patients Under Different Pathological Conditions." Fractais 15, 399 (2007).
(Continued)

*Primary Examiner* — Etsub D Berhanu
(74) *Attorney, Agent, or Firm* — Jeffrey Schox; Diana Lin

(57) ABSTRACT

A method and system for instructing a user behavior change comprising: collecting a first and a second bioelectrical signal dataset; generating an analysis based upon the first and the second bioelectrical signal datasets; and providing a behavior change suggestion to the user based upon the analysis. The method can further comprise collecting a third bioelectrical signal dataset associated with a performance of an action by the user in response to the behavior change suggestion; generating an adherence metric based upon the third bioelectrical signal dataset and at least one of the first and the second bioelectrical signal datasets; providing a stimulus configured to prompt an action by the user; and providing at least one of the analysis and an analysis based upon the adherence metric to the user. An embodiment of the system comprises a biosignal detector and a processor configured to implement an embodiment of the method.

8 Claims, 6 Drawing Sheets

Related U.S. Application Data

(60) Provisional application No. 61/652,045, filed on May 25, 2012.

(51) Int. Cl.
| | | |
|---|---|---|
| *A61B 5/00* | (2006.01) | |
| *G06F 19/00* | (2018.01) | |
| *G16H 50/20* | (2018.01) | |
| *A61B 5/0205* | (2006.01) | |

(52) U.S. Cl.
CPC ............ *G16H 50/20* (2018.01); *A61B 5/0205* (2013.01); *A61B 5/7285* (2013.01)

(56) References Cited

U.S. PATENT DOCUMENTS

| | | |
|---|---|---|
| 6,801,803 B2 | 10/2004 | Viertioe-Oja |
| 6,954,700 B2 | 10/2005 | Higashida et al. |
| 7,639,145 B2 | 12/2009 | Lawson et al. |
| 7,844,324 B2 | 11/2010 | Saerkelae et al. |
| 7,904,144 B2 | 3/2011 | Causevic et al. |
| 7,933,644 B2 | 4/2011 | Wong et al. |
| 7,962,204 B2 | 6/2011 | Suffin et al. |
| 7,986,991 B2 | 7/2011 | Prichep |
| 8,103,333 B2 | 1/2012 | Tran |
| 8,108,036 B2 | 1/2012 | Tran |
| 8,114,021 B2 | 2/2012 | Robertson et al. |
| 8,137,270 B2 | 3/2012 | Keenan et al. |
| 8,147,419 B2 | 4/2012 | Krauss et al. |
| 8,190,248 B2 | 5/2012 | Besio et al. |
| 8,190,249 B1 | 5/2012 | Gharieb et al. |
| 8,271,075 B2 | 9/2012 | Chuang et al. |
| 8,306,610 B2 | 11/2012 | Mirow |
| 8,583,223 B2 | 11/2013 | Maddess et al. |
| 8,652,040 B2 | 2/2014 | Leboeuf et al. |
| 8,688,209 B2 | 4/2014 | Verbitskiy |
| 8,690,769 B2 | 4/2014 | Edman et al. |
| 8,725,243 B2 | 5/2014 | Dilorenzo et al. |
| 8,838,215 B2 | 9/2014 | John et al. |
| 9,179,854 B2 | 11/2015 | Doidge et al. |
| 2004/0078219 A1 | 4/2004 | Kaylor et al. |
| 2004/0137639 A1 | 7/2004 | Miyazaki et al. |
| 2004/0236240 A1 | 11/2004 | Kraus et al. |
| 2005/0107723 A1* | 5/2005 | Wehman ............... A61B 5/1118 600/595 |
| 2005/0240087 A1 | 10/2005 | Keenan et al. |
| 2005/0283053 A1 | 12/2005 | Decharms |
| 2006/0009697 A1 | 1/2006 | Banet et al. |
| 2006/0015034 A1 | 1/2006 | Martinerie et al. |
| 2006/0063980 A1 | 3/2006 | Hwang et al. |
| 2007/0032737 A1 | 2/2007 | Causevic et al. |
| 2007/0061735 A1 | 3/2007 | Hoffberg et al. |
| 2007/0100246 A1 | 5/2007 | Hyde |
| 2007/0113725 A1* | 5/2007 | Oliver ............... A61B 5/02438 84/612 |
| 2007/0150025 A1 | 6/2007 | Dilorenzo et al. |
| 2008/0103368 A1* | 5/2008 | Craine ............... A61B 5/0002 600/300 |
| 2008/0177197 A1 | 7/2008 | Lee et al. |
| 2008/0194981 A1 | 8/2008 | Sarkela et al. |
| 2009/0018405 A1 | 1/2009 | Katsumura et al. |
| 2009/0024050 A1 | 1/2009 | Jung et al. |
| 2009/0062676 A1 | 3/2009 | Kruglikov et al. |
| 2009/0131764 A1 | 5/2009 | Lee et al. |
| 2009/0137923 A1 | 5/2009 | Suffin et al. |
| 2009/0214060 A1 | 8/2009 | Chuang et al. |
| 2009/0227876 A1 | 9/2009 | Tran |
| 2009/0247894 A1 | 10/2009 | Causevic |
| 2009/0318779 A1 | 12/2009 | Tran |
| 2009/0318825 A1 | 12/2009 | Kilborn |
| 2010/0010336 A1 | 1/2010 | Pettegrew et al. |
| 2010/0022820 A1 | 1/2010 | Leuthardt et al. |
| 2010/0022907 A1 | 1/2010 | Perez-Velazquez et al. |
| 2010/0094155 A1 | 4/2010 | Prichep |
| 2010/0147913 A1 | 6/2010 | Corets |
| 2010/0169409 A1 | 7/2010 | Fallon et al. |
| 2010/0286549 A1 | 11/2010 | John et al. |
| 2010/0312188 A1 | 12/2010 | Robertson et al. |
| 2011/0071364 A1 | 3/2011 | Kuo et al. |
| 2011/0087125 A1 | 4/2011 | Causevic |
| 2011/0184247 A1 | 7/2011 | Contant et al. |
| 2011/0245633 A1 | 10/2011 | Goldberg et al. |
| 2011/0270117 A1 | 11/2011 | Warwick et al. |
| 2013/0178731 A1 | 7/2013 | Bosl |

OTHER PUBLICATIONS

Stam et al., Nonlinear Synchronization in EEG and Whole-Head MEG Recordings of Healthy Subjects, date unknown.

* cited by examiner

SYSTEM AND METHOD FOR INSTRUCTING A BEHAVIOR CHANGE IN A USER

CROSS-REFERENCE TO RELATED APPLICATIONS

This application is a continuation of U.S. application derail Ser. No. 13/903,832, filed 28 May 2013, which claims the benefit of U.S. Provisional Application Ser. No. 61/652,045 filed 25 May 2012, which is incorporated in its entirety herein by this reference.

TECHNICAL FIELD

This invention relates generally to the biosignals field, and more specifically to a new and useful system and method for instructing a behavior change in the biosignals field.

BACKGROUND

The general populace interacts with a wide variety of sensors on a daily basis and vast amounts of data pertaining to individuals and entire groups of people is collected from these sensors. This data can be anchored in the physical realm, such as location data provided through a GPS sensor, caloric expenditure provided by an exercise machine, footstep count provided by an accelerometer-based step counter, or heart rate, body temperature, respiratory rate, or glucose level provided by a biometric sensor. This data can alternatively be anchored in the digital realm, such as interests as indicated by websites visited or needs as indicated by purchases made through an online store. Such data can provide significant insight into market trends and needs, interests, and expectations of a particular user or demographic. Furthermore, this data can even be used to target a user with particular experience, physical good or service, or digital good or service. However, contemporary sensors, data collection, and data analysis fail to capture cognitive, mental, and affective states of individuals and groups of people that can provide similar insight and improve user experiences and abilities. Furthermore, contemporary data collection fails to efficiently locate, obtain, and aggregate biosignal data from multiple or selected individuals and make this data available for analysis. Thus, there is a need in the biosignals field for a new and useful system and method for instructing a behavior change in a user.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1A:
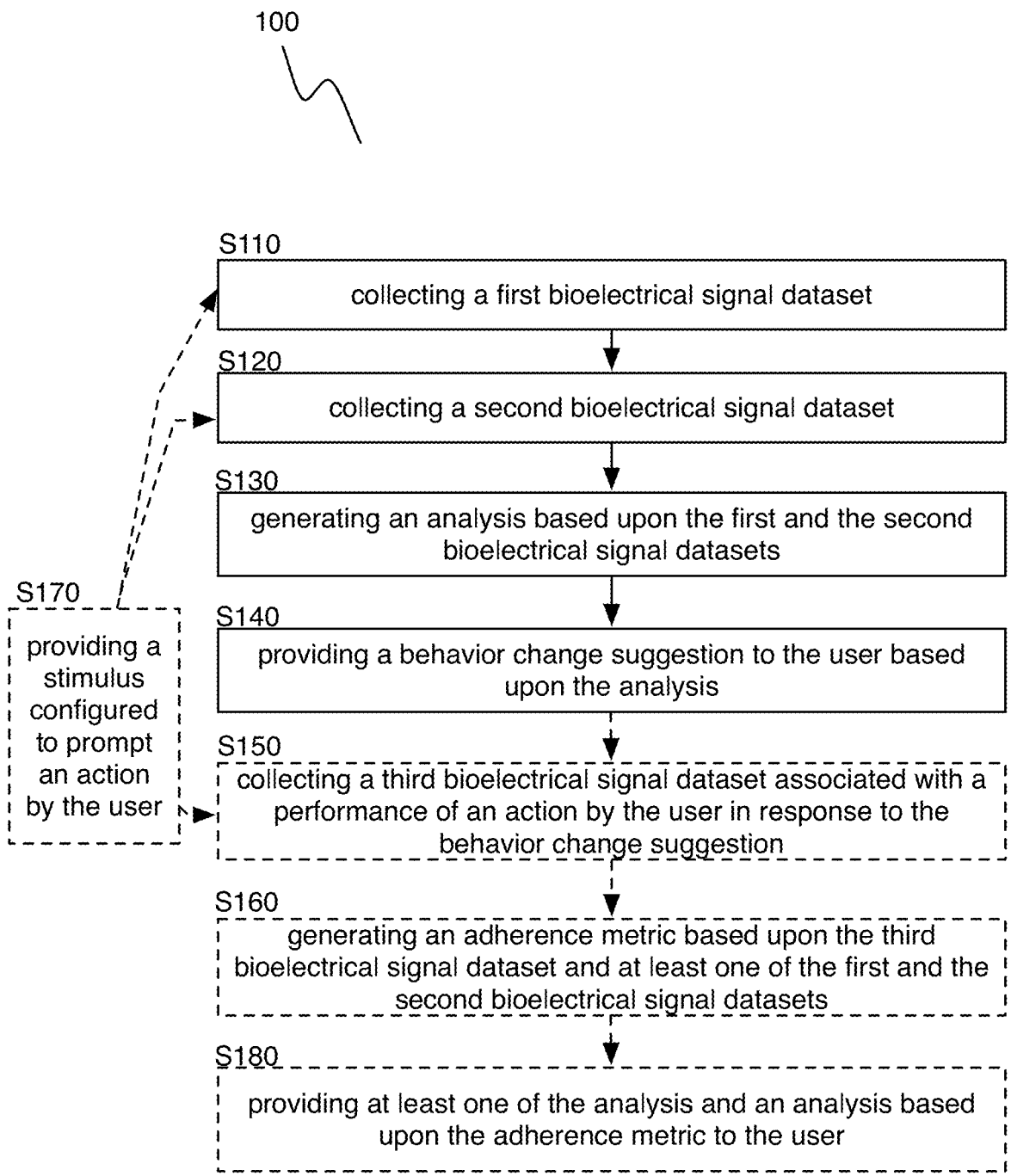
FIG. 1A is a flowchart representation of an embodiment of a method for instructing a behavior change in a user.
Figure 1B:
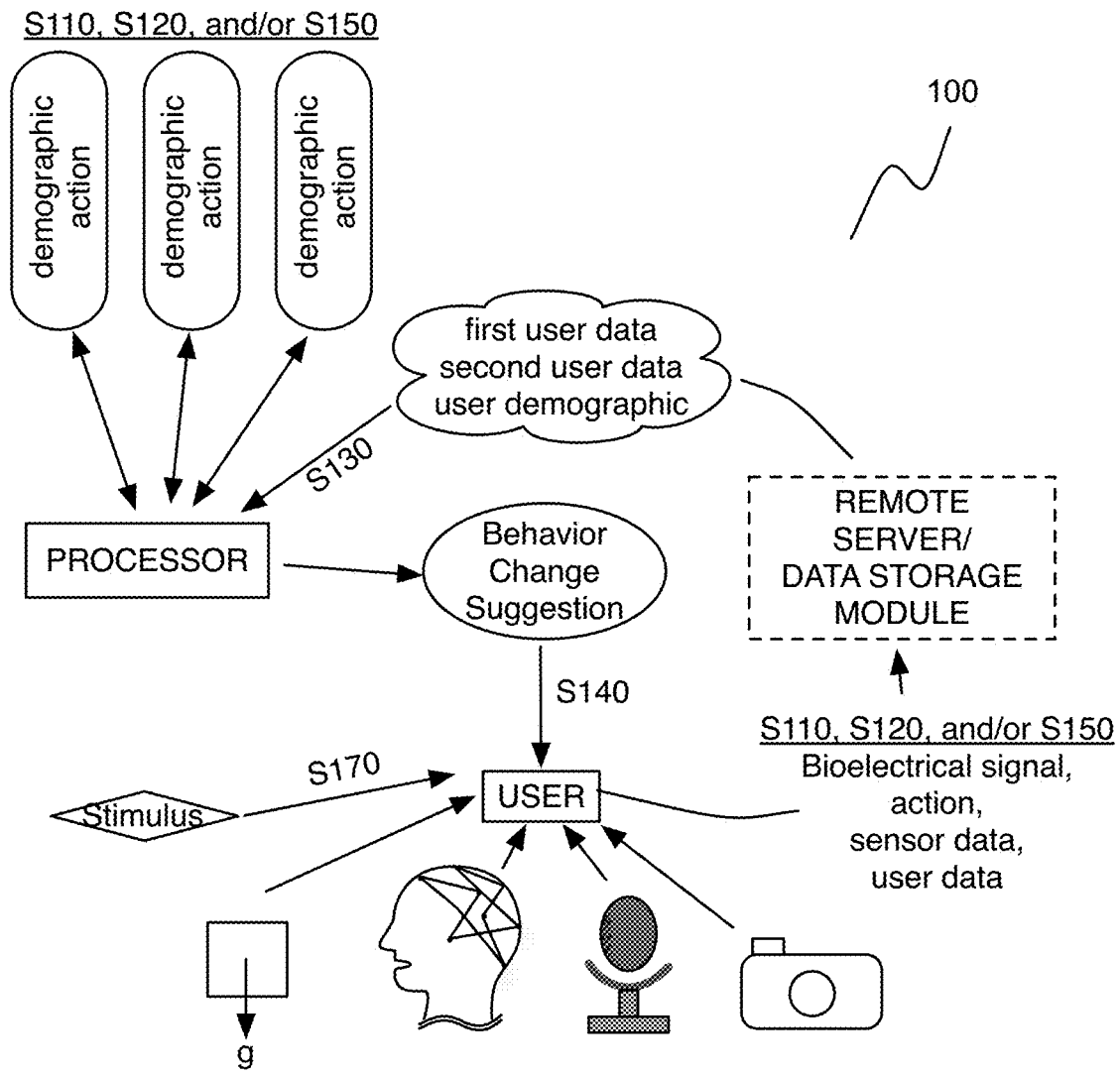
FIG. 1B is a schematic of an embodiment of a method for instructing a behavior change in a user.

As shown in FIGS. 1A and 1B, an embodiment of a method 100 for instructing a behavior change in a user comprises collecting a first bioelectrical signal dataset S110; collecting a second bioelectrical signal dataset S120; generating an analysis based upon the first bioelectrical signal dataset and the second bioelectrical signal dataset S130; and providing a behavior change suggestion to the user based upon the analysis S140. The method 100 can further comprise collecting a third bioelectrical signal dataset associated with a performance of an action by the user in response to the behavior change suggestion S150; generating an adherence metric based upon the third bioelectrical signal dataset and at least one of the first and the second bioelectrical signal datasets S160; providing a stimulus configured to prompt an action by the user S170, wherein the action is associated with one of the bioelectrical signal datasets, and providing at least one of the analysis and an analysis based upon the adherence metric to the user S180.

The method 100 functions to facilitate a behavior change in a user based upon an analysis of bioelectrical signal data received from the user while the user performs a particular action (or activity) or responds to a stimulus. The method 100 preferably functions to facilitate a behavior change in a user outside of a clinical (e.g., hospital, therapy center) or research (e.g., laboratory) environment using portable devices; however, the method 100 can additionally or alternatively function to facilitate a behavior change in any suitable environment of the user or in any suitable manner. The method 100 can further function to facilitate a behavior change in a user based upon an analysis of the user's bioelectrical signal data and other data from the user, and/or to facilitate a behavior change in a user based upon an analysis of a user's bioelectrical signal data and data from another user (or group of users). The analyses can also be performed on data collected at multiple time points and/or under different circumstances (e.g., actions or activities) from a single user or group of users.

One variation of the method 100 functions to receive electroencephalogram (EEG) data taken while the user engages in a particular action, to define trends in the user brain activity based upon comparison of the user EEG data with EEG data received from the user at an earlier time point, and to provide a behavior change suggestion to the user in order to improve or modify the cognitive, mental, and even physical well-being of the user. In this variation, EEG data of the user can be further compared against EEG data of other users ("aggregate EEG data") to further inform the behavior change suggestion. Generally, trends and changes in user brain function over time can be ascertained by tracking and comparing user EEG data, particularly EEG data of the user performing the same or similar actions. These trends and/or changes can indicate user mental development, brain "wiring," "rewiring," learning progression, or adaptation to stimuli over time and/or in comparison with other users. These trends can furthermore be used to provide the behavior change suggestions that shifts user behavior toward maximizing development of knowledge, skills, or abilities. Additionally or alternatively, these trends or changes can indicate the occurrence of a particular mental state and/or the events or process leading into a particular mental state. This variation of the method 100 can therefore access and analyze brain activity of the user to provide insight into improving or modifying the cognitive, mental, and/or physical well being of the user.

Another variation of the method 100 functions to receive bioelectrical signal data taken while the user performs a particular action in response to a provided stimulus, to define trends in the user biosignal activity based upon comparison of the user bioelectrical signal data with bioelectrical signal data received from the user at an earlier time point and associated with an earlier instance of stimulus provision, and to provide a behavior change suggestion to the user in order to improve or modify the response of the user to the stimulus. In this variation, the method 100 can function to hone or modify a user's response or reaction to a stimulus, thus affecting a behavior change in order to promote the well-being of the user.

In a few specific applications of the variations, the method 100 can be used to facilitate a behavior change to increase productivity in a working environment, or used to adjust a behavioral response of a user suffering from post-traumatic stress disorder (PTSD). The method 100 is preferably performed using an embodiment of a system 300 comprising a biosignal detector 310 and a processor 320 comprising a receiver 330, an analyzer 340, a transmitter 350, and a stimulus transmission module 360, as described in further detail below; however, the method 100 may be performed using any suitable system configured to collect bioelectrical signal data from a user and generate an analysis based upon the bioelectrical signal data.

Step S110 recites collecting a first bioelectrical signal dataset, and functions to receive data while a user performs an action relevant to a change in the user's behavior or a behavior being modified. Preferably, the bioelectrical signal data includes electroencephalograph (EEG) data, which can be reflective of cognitive, mental, and affective state of the user. However, the bioelectrical signal data can additionally or alternatively include any one of more of: data related to magnetoencephalography (MEG) impedance or galvanic skin response (GSR), electrocardiography (ECG), heart rate variability (HRV), electrooculography (EOG), and electromyelography (EMG). Furthermore, Step S110 can comprise collecting other biosignal data, including data related to cerebral blood flow (CBF), optical signals (e.g., eye movement, body movement), mechanical signals (e.g., mechanomyographs) chemical signals (e.g., blood oxygenation), acoustic signals, temperature, respiratory rate, and/or any other data obtained from or related to biological tissue or biological processes of the user, as well as the environment of the user. Additionally, the bioelectrical signal data preferably includes data acquired from multiple channels, wherein each channel is associated with a particular sensor arranged on a particular location or region of the user (e.g., head region, torso region). In one example, one of more sensors can therefore be primarily associated with a particular region of the brain, such as the left or right frontal, temporal, parietal, or occipital lobe of the cerebral cortex. The bioelectrical signal data can alternatively comprise a single signal (e.g., from a single channel or as a composite of multiple channels), or a plurality of composite signals, each of which is a composite of multiple channels. The bioelectrical signal can also be a compressed, filtered, analyzed, or otherwise processed version of raw bioelectrical signals from one or more sensors. However, the bioelectrical signal data can be of any other suitable form or format.

Figure 2:
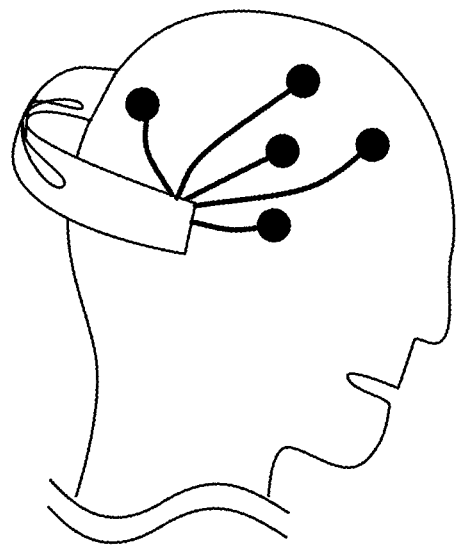
FIG. 2 depicts an embodiment of a biosignal detector.

In Step S110, collecting a first bioelectrical signal dataset preferably comprises collecting a first bioelectrical signal dataset at a biosignal detector that is worn by the user while he/she performs the action defined in Step S110. In one variation, Step S110 is performed using a portable biosignal detector that can operate outside of a clinical (e.g., hospital) or research (e.g., laboratory) setting, such that that the first user can be in a non-contrived environment as the bioelectrical signal dataset is collected and received. In another variation, Step S110 can be performed using a biosignal detector operating within a clinical or research setting. In a specific example of Step S110, the user wears a portable EEG device, an example of which is shown in FIG. 2, while performing a substantially normal, everyday activity, such as driving, playing a sport, shopping, working, studying, drawing reading, watching television, playing an instrument, or otherwise engaging in a substantially normal (e.g., daily) activity or action. In the specific example, the bioelectrical signal data (i.e., EEG signal data) is therefore collected while the user is outside of a hospital, lab, or purely medical setting and substantially removed from medical/research staff.

Furthermore, in Step S110, the bioelectrical signal dataset can be collected as described above and stored locally prior to generating an analysis in Step S130 and/or an adherence metric in Step S160, or can be stored on a separate device in communication with the biosignal detector. In variations, the separate device can be a mobile electronic device, such as a smartphone, a tablet, a personal data assistant (PDA), a laptop, or a digital music player. In other variations, the separate device can be a non-mobile device, such as a desktop computer, a gaming console, or any other suitable device. The separate device in these variations is preferably Internet-capable (e.g., via a Wi-Fi, cellular, or Ethernet connection) such that the bioelectrical signal dataset can be subsequently transmitted to a data storage module, and can be accessed by a user or other entity; however, the bioelectrical signal dataset can be accessible in any other suitable manner. By accessing the bioelectrical signal dataset following recordation, the user or other entity can associate an action, activity, person, location, mood, weather, or other relevant personal or action-related information with the bioelectrical signal data. In a specific example, this information is automatically captured through a smartphone device that stores bioelectrical signal data (e.g., EEG data) locally, through a mobile application executing on the smartphone and in communication with the data storage module. In another specific example, the user provides any of the foregoing personal or action-related information (or subsets of information) through a web browser or application executing on a non-mobile electronic device and in communication with the data storage module or through another venue, media, or method.

In Step S110, the first bioelectrical signal dataset is preferably collected from a user while the user engages in or performs an action associated with the behavior change. In one variation, the action comprises the behavior being modified; however, in other variations, the action alternatively comprises actions complementary to, opposed to, or substantially different from the behavior being modified. In one specific example of Step S110, the action and the behavior being modified comprise playing an instrument, such that the method 100 provides an analysis and/or behavior change suggestion that can improve the user's ability to play the instrument. In another specific example of Step S110, the action comprises performing a difficult task that the user has mastered, and the behavior being modified comprises performing a difficult task that the user has not mastered, such that the method 100 provides an analysis and/or behavior change suggestion that can help the user master the task that he or she has not mastered. In another specific example of Step S110, the action comprises surfing the web and the behavior being modified relates to working productively, such that the method 100 provides an analysis and/or behavior change suggestion based upon non-productive working activities in order to increase working productivity.

Furthermore, collecting a bioelectrical signal dataset in Step S110 can be triggered manually or automatically, as described in the following variations. In a first variation, receiving the bioelectrical signal dataset is triggered manually. In a first example of the first variation, the user activates a biosignal detector prior to performing an action related to the user's behavior change or the behavior being modified, for example, by depressing a 'record' button, setting a timer to begin recording, and/or providing any other input to activate the biosignal detector. In a second variation, receiving the bioelectrical signal dataset is triggered automatically. In a first example of the second variation, an accelerometer integrated into the biosignal detector can sense accelerations of the first user, enabling anticipation of the action of the first user based upon an accelerometer signal (e.g., predominantly vertical accelerations and small forward accelerations with peaks occurring at a frequency of approximately 2 Hz indicate that the user is walking, triggering bioelectrical signal capture). In a second example of the second variation, a camera proximal to the user cooperates with a processor implementing machine vision to determine objects or people proximal to the user, wherein the processor determines the user to be reading when an image depicts an open book in front of the first user, triggering bioelectrical signal capture. In a third example of the second variation, a digital calendar of the user is accessed, wherein events on the calendar, including dates, times, and event descriptions, indicate an anticipated action of the first user at a particular time, triggering bioelectrical signal capture at the particular time. In a fourth example of the second variation, a biometric sensor coupled to the user collects biometric data (e.g., heart rate data, blood oxygen level data, and respiratory rate data) of the first user, which is correlated to a particular action (e.g., by a processor), triggering bioelectrical signal capture. However, any other sensor coupled to, in communication with, or integrated into a biosignal detector or data storage module can function independently or in cooperation with any other sensor or processor to estimate an action of the first user to trigger bioelectrical signal capture. Through the foregoing examples or any other example of signal capture and analysis, an action of the user can be automatically detected and used to initiate bioelectrical signal capture in Step S110. However, the action of the user can be indicated or determined in any other way or used to initiate and/or terminate bioelectrical signal capture in any other way. For example, a camera may detect a closed book suggesting that the user has finished reading, which terminates bioelectrical signal collection.

In a further variation of Step S110, an action tag defined by the user can initiate bioelectrical signal data collection semi-automatically. The action tag is preferably provided through an interface device, such as a smartphone, tablet, or other electronic device. Additionally or alternatively, action tags defined by the user can be added to the bioelectrical signal data to inform an action performed by the user during the related bioelectrical signal capture session. In one example, an input provided by the user into an e-reader to move to a subsequent page indicates that the user is reading; and the title, genre, and/or other details of the book can also be accessed. In another example, a user input into an electric piano (or acoustic piano with a built-in touch or audio sensor) indicates that the user is playing the piano; and the particular piece can be also identified and the skill level of the piece can be estimated. In another example, a user input into a television remote control indicates that the user is watching television; and the particular show, movie, or sporting event can also be determined, such as by accessing a television calendar. In yet another example, a GPS sensor arranged within a vehicle determines that the user is driving and provides information related to the departure and present locations, from which a final destination and local traffic conditions can also be assembled, such as by accessing published traffic data and an electronic calendar of the user. In still another example, a device for administration of an aptitude test or neuropsychological test can supply information related to presentation and timing of questions, tasks, and other stimuli, including overall performance or performance on individual questions or tasks. However, any other device implementing any other sensor can be accessed to inform the action of the user and to initiate and/or terminate bioelectrical signal capture.

Again, any one or more of the aforementioned sensors, or any other sensor coupled to, in communication with, or integrated into a biosignal detector collecting bioelectrical signal data, or coupled to a bioelectrical signal storage module can define an action tag for the bioelectrical signal data collected in Step S110. Additional information associated with the action and sourced from external entities, such as the title of a book read by the user, can also be associated with the bioelectrical signal data. The user can also provide information pertaining to the user himself/herself, the action, or environmental conditions proximal to the action. Therefore, information of various types and provided by various sources can enrich and augment bioelectrical signal data that is collected in Step S110. Additionally or alternatively, the bioelectrical signal data and enriching data can be added to compiled bioelectrical signal data of multiple users, and in this variation, the bioelectrical signal data and enriching data are preferably anonymized to conform to relevant privacy and security laws, such as the Health Insurance Portability and Accountability Act (HIPAA).

Figure 3:
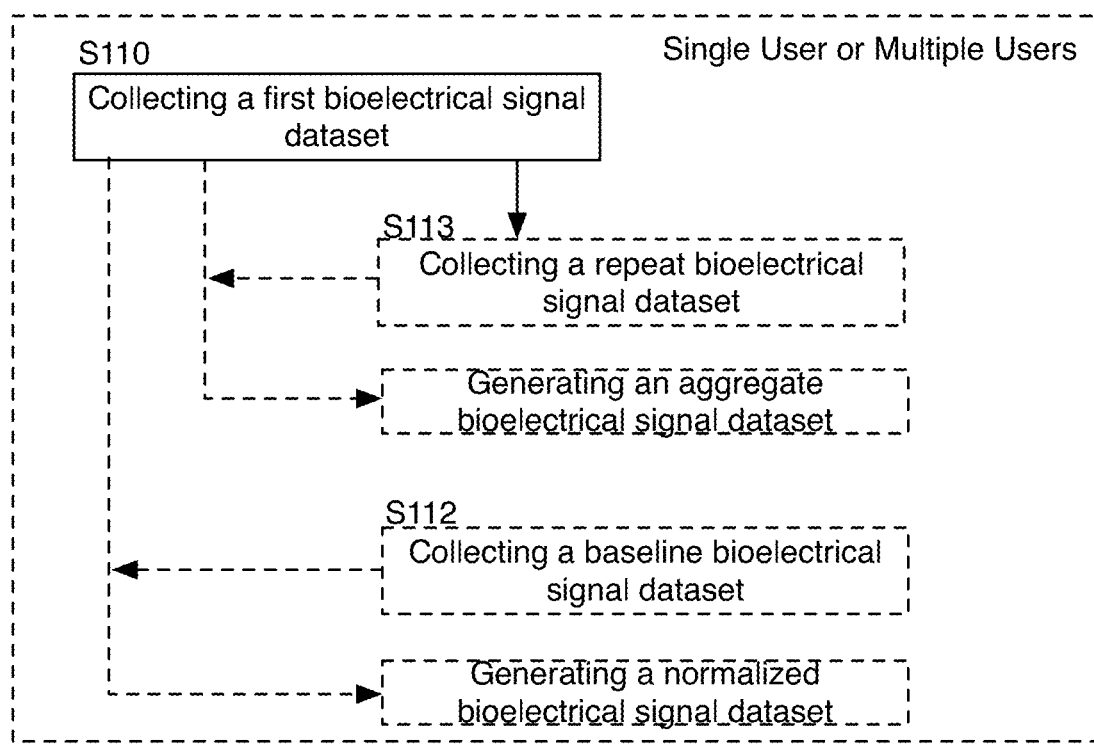
FIG. 3 is a flowchart representation of an embodiment of a portion of a method for instructing a behavior change in a user.

As described above in the variations and examples of Step S110, receiving the first bioelectrical signal dataset preferably includes receiving bioelectrical signal data taken while the user performs an action; however, as shown in FIG. 3, Step S110 may further include collecting a baseline bioelectrical signal dataset S112 and/or collecting a repeat bioelectrical signal dataset S113 substantially near in time to the time window during which the first bioelectrical signal dataset is received. Collecting a baseline bioelectrical signal dataset can comprise collecting bioelectrical signal data while the user is in a neutral state, and functions to generate a baseline dataset against which other bioelectrical signal data from a user can be normalized or compared (e.g., to produce a normalized bioelectrical signal dataset). In a specific example of collecting a baseline bioelectrical signal dataset, a set of EEG data can be taken while the user is stationary with eyes closed for a period of time (e.g., thirty seconds) prior to collecting bioelectrical signal data while an action is being performed (e.g., between an action initiation time point and an action termination time point). However, the baseline bioelectrical signal dataset can be of any other suitable active or passive action of the user and the EEG signal can include any other relevant EEG data. Collecting a repeat bioelectrical signal dataset functions to allow multiple bioelectrical signal datasets from a user to be collected and analyzed (e.g., to produce an aggregate bioelectrical signal dataset for a single user or multiple users). The repeat bioelectrical signal dataset(s) can be collected while a user repeats a specific action, such that multiple datasets characterizing a substantially identical action can be analyzed to facilitate a behavior change; however, the bioelectrical signal dataset can be collected while the user performs a different action than a previously performed action. In one example, the first bioelectrical signal dataset can be collected while the user is listening to music, and the repeat bioelectrical signal dataset can be collected while the user is playing an instrument, such that data for complementary actions can analyzed to facilitate a behavior change. In another example, the first bioelectrical signal dataset can be collected while the user is mentally focused on a working task and the repeat bioelectrical signal dataset can be collected while the user is distracted, such that data for "opposite" actions can be analyzed to facilitate a behavior change. In this example, bioelectrical signal datasets associated with an action, paired with repeat bioelectrical signal datasets associated with a different action, acquired at substantially different time points (e.g., in Steps S110 and S120) can be analyzed for divergences in signal trends for the two actions, across the time points, as an indication of behavior change.

Step S120 recites collecting a second bioelectrical signal dataset, and functions to provide data that can be analyzed with the first bioelectrical dataset to form a behavior change suggestion. Similar to Step S110, Step S120 is preferably performed while a user performs an action relevant to a change in the user's behavior or a behavior being modified. In some variations, however, collecting bioelectrical signal datasets in Steps S110 and S120 may be performed at a single biosignal detector, or at a first biosignal detector for Step S110 and at a second biosignal detector for Step S120. Additionally, Step S110 is preferably performed within a first time window and Step S120 is preferably performed within a second time window, wherein the first time window and the second time window are substantially non-overlapping; however, the first time window and the second time window can overlap or coincide with each other in some variations, and especially in variations wherein Steps S110 and S120 involve different users.

In a first variation, Step S110 comprises collecting the first bioelectrical signal dataset during performance of a first action, and Step S120 comprises collecting the second bioelectrical signal dataset during performance of a second action that is different from the first action. The first action and the second action in this variation can be complementary actions, opposite actions, or different actions by any other suitable definition. In one example, the first bioelectrical signal dataset can be collected during one form of exercise (e.g., yoga), and the repeat bioelectrical signal dataset can be collected during another form of exercise (e.g., weight lifting), such that data for complementary actions can analyzed to improve a user's mind-body awareness in multiple forms of exercise. In another example, the first bioelectrical signal dataset can be collected during a working task (e.g., performing an engineering calculation) and the second bioelectrical signal dataset can be collected during a period of distraction, such that data for "opposite" actions can be analyzed to improve a user's mental focus at work.

In a second variation, Step S110 comprises collecting the first bioelectrical signal dataset during performance of an action (or actions) within a first time window, and Step S120 comprises collecting the second bioelectrical signal dataset during performance of the action (or actions) within a second time window. In this variation, identical (or similar) actions characterized by a first and a second bioelectrical signal dataset can be used to generate an analysis of the signal data associated with the action across time. In this variation, identical (or similar) groups of actions characterized by a first and a second bioelectrical signal dataset can also be used to generate an analysis of the signal data associated with the action group across time (e.g., an analysis of divergence or convergence between signals associated with different actions across time). In a first example, the action associated with the first and the second bioelectrical signal dataset comprises falling asleep, and the method 100 functions to facilitate a change in a user's ability to regulate his/her sleeping behavior. In a second example, the action group associated with the first and the second bioelectrical signal dataset comprises playing an easy piano piece and playing a difficult piano piece, such that the method 100 functions to enhance a user's ability to pick up difficult pieces (based upon convergences in signal data for the actions over time).

In a third variation, Step S110 comprises collecting the first bioelectrical signal dataset from a first user (or group of users), and Step S120 comprises collecting the second bioelectrical signal dataset from a second user (or group of users). Thus, in the third variation data from similar users (e.g., users in a similar demographic group) and/or different users can be used to facilitate a behavior change in a user. In a first example, the first bioelectrical signal dataset can be collected from a group of users without dyslexia during a reading activity and the second bioelectrical signal dataset can be collected from a user diagnosed with dyslexia, in order to provide suggestions to the user with dyslexia to improve his/her condition. In a second example, the first and second bioelectrical signal datasets can be collected from users of the same demographic (e.g., age, ethnicity, gender, etc . . . ), such that comprehensive bioelectrical signal data from the demographic can be used to facilitate a behavior change in at least one of the users of the demographic.

In a fourth variation, Step S110 comprises collecting the first bioelectrical signal dataset from a user within a first time window, and Step S120 comprises collecting the second bioelectrical signal dataset from the user during a second time window. The fourth variation therefore enables analyses to be generated based upon a time-series of bioelectrical signal data taken from the same user, in order to facilitate a behavior change.

Figure 4:
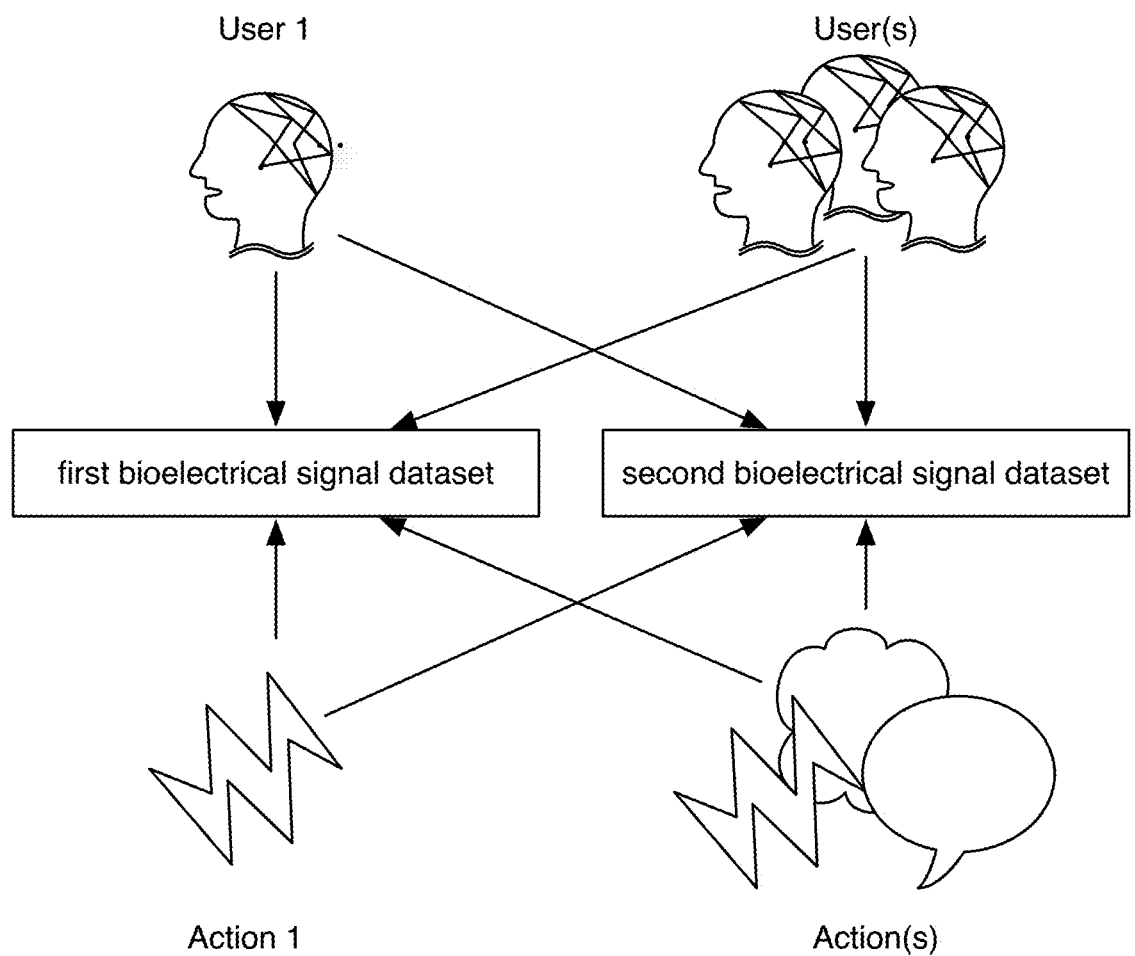
FIG. 4 is a flowchart representation of an embodiment of a portion of a method for instructing a behavior change in a user.

Thus, as shown in FIG. 4, variations of Steps S110 and S120 encompass conditions wherein the first and the second bioelectrical signal datasets are collected from the same user or different users, and/or are associated with the same or different action(s). Additionally, Steps S110 and S120 can be performed according to any of the embodiments, variations, examples, or any combination thereof as described in U.S. patent application Ser. No. 13/903,806, entitled "System and Method for Providing and Aggregating Biosignals and Action Data", which is incorporated herein in its entirety by this reference.

Figure 5:
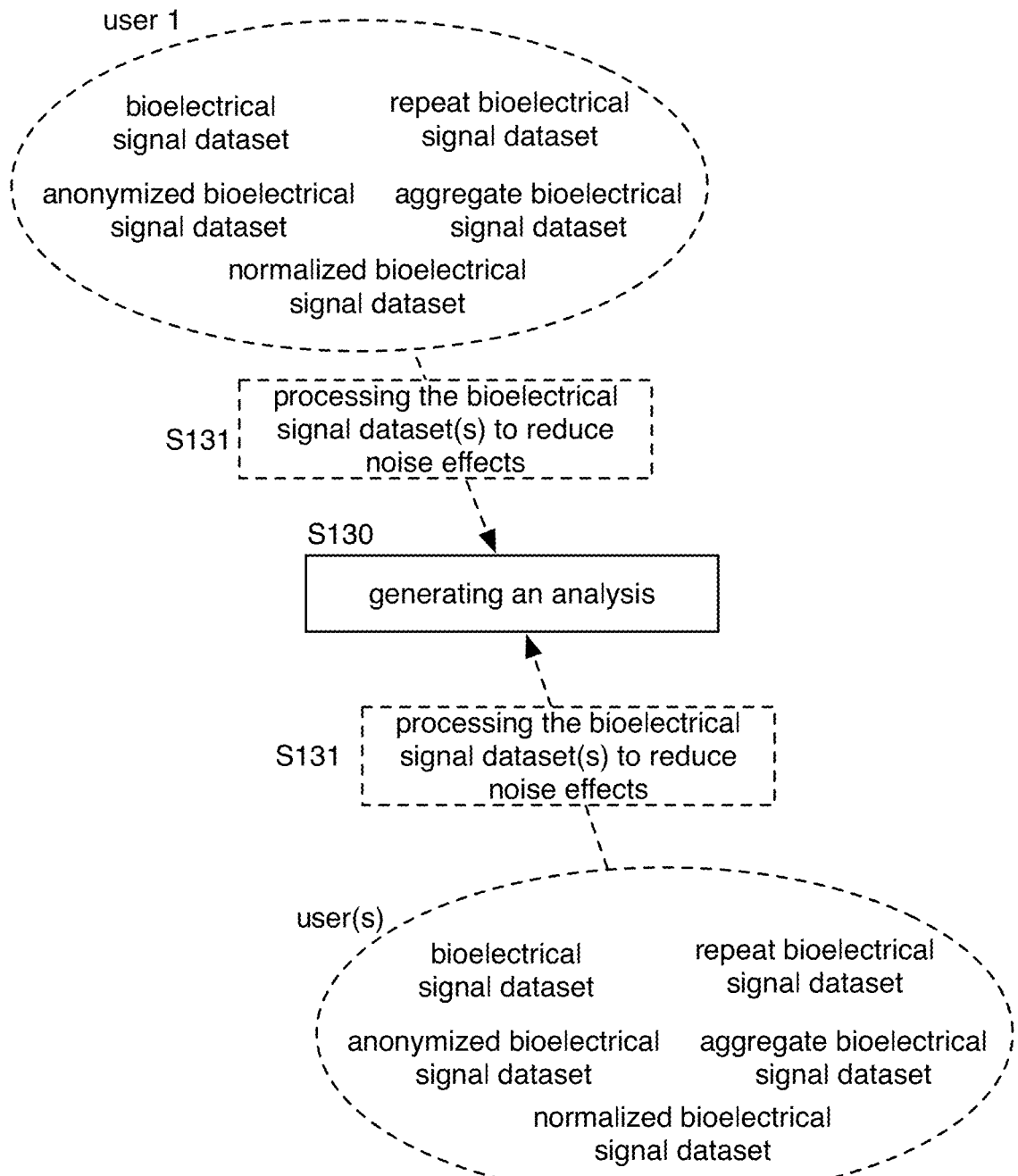
FIG. 5 is a flowchart representation of an embodiment of a portion of a method for instructing a behavior change in a user.

Step S130 recites generating an analysis based upon the first bioelectrical signal dataset and the second bioelectrical signal dataset, and functions to form the basis of a behavior change suggestion that can modulate a user's behavior. As shown in FIG. 5, Step S130 can further comprise processing the first bioelectrical signal dataset and/or the second bioelectrical signal dataset to reduce noise effects S131. In one variation, processing can comprise filtering, compressing, analyzing, or comparing multiple bioelectrical signal datasets, taken within multiple time windows, against baseline bioelectrical signal data to reduce noise. A first variation of Step S130 can comprise comparing a first bioelectrical signal dataset from a user with a second bioelectrical signal dataset from the user to extract information related to trends in signals correlated, for example, with different brain regions. In one example, brain activity, as characterized by EEG signal data, can be isolated for general regions of the brain, such as the forebrain, midbrain, and hindbrain, for particular regions of the brain, such as the frontal, temporal, parietal, or occipital lobe of the cerebral cortex, for more specific portions of the brain, such as the left or right parietal lobe, or for any other portion of the brain of any other focus. Brain activity can also be isolated indicating functional connectivity or interaction between multiple portions of the brain. Stimuli and actions, such as playing a piano, reading a book, watching a commercial or sporting event, eating, studying, drawing, cooking, talking with friends, etc., can then be associated with brain activity in a particular portion of the brain. A multidimensional matrix of stimulus, action, environmental condition, related user experience, etc. over time can be assembled to quantitatively and/or qualitatively relate certain brain activity to a particular user experience and to depict changes in user brain activity over time given the particular user experience. Additionally, comparing bioelectrical signal data taken at multiple time points and associated with similar actions can further allow trends in brain activity over time (e.g., over days, weeks, or years) to be extracted despite signal noise.

In the first variation of Step S130, generating an analysis based upon a comparison of the first and the second bioelectrical signal dataset can show how the brain of the user is changing and adapting over time. For example, a trend in increased brain activity in the right frontal lobe and the parietal lobe while painting can be associated with increased creative function in the frontal lobe and improved deftness of motion (or "muscle memory") as controlled by the parietal lobe. In this example, an analysis generated in Step S130 can provide the basis of a behavior change suggestion in Step S140 that advises the user to continue a drawing regimen that has been shown, by the analysis, to yield positive changes in brain function related to drawing ability. Similarly, a lack of significant change in brain activity over time, based upon an analysis generated in Step S130, can indicate that the brain is not changing or adapting to a stimulus or input. For example, an increase and then taper in user brain activity while playing the piano can suggest a period of positive learning followed by a period in which a user skill (as related to brain function) shows limited improvement. In this example, the analysis of Step S130 can be used to generate a behavior change suggestion in Step S140 that advises a user to change a style of learning the piano or to increase the difficulty of pieces played during piano practice. Furthermore, in this example, sensors in the piano (e.g., a microphone, accelerometer, or piezoresistive element) can record user inputs into the piano such that actual skill level of the user can be correlated with brain activity or trends in brain activity over time. Changes in brain function can therefore be extrapolated from trends in brain activity to indicate a level of user improvement in a skill or capability.

Additionally or alternatively in Step S130, the analysis can detect occurrences of a particular mental state (e.g., as typified by elevated brain activity or function in a particular portion of the brain) which can be associated with a stimulus, action, environmental condition, etc. leading into the particular mental state. For example, the user can indicate a feeling of being "in the zone" at a certain time in which EEG data shows high activity in the left frontal lobe and extremely limited activity in other portions of the brain. A unique brain activity fingerprint for such a mental state can thus be generated. Additionally or alternatively in Step S130, a (time-lapse) brain activity fingerprint leading up to realization of the particular mental state can also be generated, and certain brain activities can be linked to particular user actions in the analysis generated in Step S130. In an example, a recipe for entering the particular mental state can thus be assembled, wherein this recipe can be unique to the user or general to a group of users or particular demographic. At least one of the brain activity fingerprint and the mental state recipe can further be provided to the user in Block S140 as a behavior change suggestion, which can aid the user in returning to the desired mental state. However, any other brain function can be extrapolated from trends in brain activity and used to isolate a particular mental state, skill, or ability of the user.

A second variation of Step S130 can comprise generating an analysis based upon comparing a bioelectrical signal dataset from a first user with bioelectrical signal data of at least one other user. The bioelectrical signal data of the at least one other user is preferably incorporated into aggregate bioelectrical signal data maintained by a data storage module as described briefly above and in further detail below. Comparing bioelectrical signal data of the first user with aggregate bioelectrical signal data from other users in the second variation of Step S130 can provide a benchmark for user progress or changes in brain activity. The speed at which the brain of the user adapts to a new stimulus, the volume of brain activity in a certain portion of the brain for a given activity or stimulus, retention of brain activity levels for a given activity or stimulus over time, or any other relevant metric of user brain function can be compared with all or portions of the aggregate bioelectrical signal data, such as for users of a demographic, skill level, or experience level similar to that of the user. Additionally or alternatively, comparing user and aggregate bioelectrical signal data in the second variation of Step S130 can inform a process by which the first user can enter a previously-unavailable or difficult-to-achieve mental state, such as by suggesting a mental state recipe of another user to the user in a variation of Step S140. However, comparing user and aggregate bioelectrical signal data can inform any other relevant metric, standard, or benchmark or aid development of user brain function in any other way.

Step S130 can thus comprise generating an analysis based upon data including bioelectrical signal data and other data (e.g., biosignal, biometric, and environment data), data associated with one action or multiple actions (e.g., to determine a convergence or divergence in signals associated with multiple actions), and data collected from a single user or multiple users (e.g., aggregate bioelectrical signal data). The analysis can further be generated according to any suitable combination of the embodiments, variations, and examples described above, using independent components analysis, or using any suitable method, such as those described in U.S. Pat. Pub. No. 2013/0035579, entitled "Methods for Modeling Neurological Development and Diagnosing a Neurological Impairment of a Patient", which is incorporated herein in its entirety by this reference.

As shown in FIGS. 1A and 1B, Step S140 recites providing a behavior change suggestion to the user based upon the analysis generated in Step S130. The suggestion is preferably related to one or more actions that stimulates brain activity in the user and/or induces a mental state of the user. In one variation of Step S140, the behavior change suggestion includes urging the user to engage in a particular activity more often because trends in user brain activity indicate a correlation between positive brain development and the activity. For example, trends in bioelectrical signal data for a user who is autistic can correlate viewing images of faces, such as in a magazine or on a television, with reduced brain activity in the frontal lobe of the user, wherein such higher levels of activity in this part of the brain is associated with user discomfort or nervousness. In this example, providing the behavior change suggestion in Step S140 can include urging the user to spend more time viewing images of faces in magazines or on television based upon an analysis generated in Step S130.

In another variation of Step S140, the behavior change suggestion includes urging the user to engage in a particular activity that is shown in other users to improve brain function (based upon an analysis generated for multiple users). For example, aggregate bioelectrical signal data of stroke victims can correlate gains in brain function in an affected brain area with painting or sketching. In this example, providing the behavior change suggestion in Step S140 can therefore include urging the user who is a stroke victim to paint or to sketch based upon an analysis generated in Step S130.

In yet another variation of Step S140, the behavior change suggestion includes urging the user to modify a behavior. For example, and as described above, reduced or tapering brain activity when playing a piano can prompt the behavior change suggestion provided in Step S140 to include urging the user to modify a style of learning or increase the difficulty of practice pieces. In another example, a trend in user and/or aggregate bioelectrical signal data indicates that brain activity and brain development improve at more rapid rates for users reading paper-format media than for users reading digital-format media. In this example, providing the behavior change suggestion in Step S140 can therefore include offering a paper-based substitute for the user viewing digital media. In a further example, a trend in user bioelectrical signal data shows that the user exhibits substantially isolated and elevated activity in the left frontal lobe, which is correlated with increased efficiency and work quality, when working on a computer that is disconnected from the Internet. Furthermore, in this example, an analysis based upon the bioelectrical signal data indicates reduced activity in the left frontal lobe, which is correlated with reduced efficiency and work quality, while working on a computer that is connected to the Internet. In this example, providing the behavior change suggestion in Step S140 can therefore include reducing or restricting Internet access and limiting other distractions available on the user's computer while working.

The behavior change suggestion of Step S140 is preferably provided directly to the user. However, the behavior change suggestion can additionally or alternatively be provided to a parent or legal guardian, a teacher, a physician or other doctor, an employer, or any other suitable entity related to or interacting with the user. The parent or legal guardian can implement the behavior change suggestion to improve disciplinary action, teaching, care, or other interactions with the user who is a child. The teacher can implement the behavior change suggestion to modify a curriculum, a teaching style, a mentoring role, a teacher-student and/or student-student interaction, or any other teaching-related variable for the user who is a student. The physician can implement the behavior change suggestion to prescribe an action, an intervention, a medication, or a therapy for the user who is a patient. The employer can implement the behavior change suggestion to change a workspace layout, an employer-employee or employee-employee interaction, work content or workflow, a deadline, or any other employment-related variable for the user who is an employee. However, any other entity can access the behavior change suggestion and implement any other change in response to the behavior change suggestion provided in Step S140. Furthermore, the parent or legal guardian, teacher, physician or other doctor, employer, or other entity can also be instrumental in generating the behavior change suggestion, such as by providing additional user-related information to a data storage module or the third-party entity to inform the behavior change suggestion. Alternatively, the entity can generate the behavior change suggestion directly by accessing and analyzing available user bioelectrical signal data trends and/or aggregate bioelectrical signal data. The behavior change suggestion preferably informs a behavior or action that moves the user toward optimizing learning or development of new knowledge or a new skill or ability.

In some variations, the behavior change suggestion of Step S140 can be provided to the user (or other entity) through a mobile application executing on a mobile electronic device, such as the same mobile electronic device that handles distribution of bioelectrical signal data from a biosignal detector (that collects bioelectrical signal data) to a data storage module. The behavior change suggestion can additionally or alternatively be provided through a web browser executing on an electronic device associated with or distinct from user bioelectrical signal data distribution. However, the behavior change suggestion can additionally or alternatively be provided through an email client, an electronic calendar, or any other suitable user interface or any other suitable device. In these variations, the behavior change suggestion can be presented as a notification, a calendar event, an email, a chart or other visual media depicting bioelectrical signal data (and associated action) data or trends, or in any other suitable format or combination of formats.

In other variations, the behavior change suggestion provided in Step S140 can be automatically implemented at a device associated with a user (e.g., mobile device, biometric monitor) or at a device that modifies aspects of the user's environment. In one example, for a user suffering from a sleeping disorder, lighting, room temperature, and ambient sound within the user's environment can be automatically adjusted (as a behavior change suggestion) based upon an analysis of the user's brain activity and desired sleeping behavior. In another example, for a user suffering from fatigue, the behavior change suggestion can comprise automatic enforcement of a "resting period" (e.g., automatic saving, shutdown, and period of disablement of software applications associated with work). In yet another example, for a user suffering from depression, the behavior change suggestion can comprise automatically restricting the accessibility of certain materials (e.g., household items that can be abused, which are stored in an electronically lockable container) for the user based upon an analysis that shows that the user is entering a depressive or anxious phase. These variations can additionally or alternatively comprise automatically implementing a behavior change suggestion using any other suitable method.

As shown in FIGS. 1A and 1B, the method 100 can further comprise Step S150, which recites collecting a third bioelectrical signal dataset associated with a performance of an action by the user in response to the behavior change suggestion. Step S150 functions to generate additional data that can be used to assess changes in a user's behavior based upon the user's response to the behavior change suggestion. The third bioelectrical signal dataset is preferably collected within a time window shortly after the behavior change suggestion is provided in Step S140; however, the third bioelectrical signal dataset can be collected at any suitable time after the behavior change suggestion is provided. Collection of the third bioelectrical signal dataset in Step S150 can be performed in a manner similar to that described in the descriptions of Steps S110 and S120 above, or in any other suitable manner. In some variations, collecting the third bioelectrical signal dataset can be automatically initiated upon detection of the user's performance of an action in response to the behavior change suggestion. In these variations, automatic collection can be initiated by any suitable input (e.g., sensor input) that indicates that the action is being performed and/or terminated by any suitable input that indicates that performance of the action is complete. Furthermore, variations of Step S150 can comprise initiating collection of the third bioelectrical signal dataset upon provision of the behavior change suggestion, such that additional data encompassing the user's activity between receiving the behavior action through performance of the action can be collected. Step S150 can, however, comprise any other suitable duration of data collection and can be initiated and/or terminated using any other suitable method.

The method can also further comprise Step S160, which recites generating an adherence metric based upon the third bioelectrical signal dataset and at least one of the first and the second bioelectrical signal datasets. Step S160 functions to provide an assessment of a user's adherence to the behavior change suggestion in order to measure behavior change progress. Step S160 can further function to assess the appropriateness or effectiveness of the behavior change suggestion that was provided to the user in Step S140. The adherence metric preferably provides a quantitative metric characterizing the user's adherence to the behavior change suggestion, as assessed between the third bioelectrical signal dataset and at least one of the first and the second bioelectrical signal datasets, but may alternatively be a qualitative metric. In a first example, the adherence metric characterizes improvement, stagnation, or regression in a user's behavior, and can be used to create a modified behavior change suggestion that is presented to the user. In the first example, the adherence metric can provide a regional and/or global analysis of brain activity prior to and after receiving the behavior change suggestion, wherein regional and/or global changes in activity indicate changes in behavior and/or adherence to the behavior change suggestion.

In some variations, Step S160 can further function to provide a metric for social comparisons, in order to further facilitate behavior change by the user. In these variations, the adherence metric can be provided to the user along with an adherence metric determined based upon data from at least one other user (e.g., of the same or a relevant demographic). In a specific example involving a group of users (e.g., employees) from the same company, the adherence metric can be presented to a single employee alongside an adherence metric determined from multiple employees of the same company, in order to promote changes in working efficiency at the company. However, any other suitable method of providing a social comparison based upon the adherence metric(s) can be used in other variations of Step S160.

The method can also further comprise Step S170, which recites providing a stimulus configured to prompt an action by the user S170. Step S170 functions to prompt the user to perform an action or to stimulate a reaction by a user that is associated with at least one of the bioelectrical signal datasets collected in variations of Steps S110, S120, and S150. The stimulus can be provided or deployed in any suitable manner, can be automatically or manually provided, and can be provided to multiple users (e.g., a demographic group) simultaneously or non-simultaneously. Furthermore, multiple stimuli can be deployed, such that responses to combined stimuli and/or a sequence of stimuli can be later analyzed. The stimulus can be a notification, a command to perform an action, a haptic stimulus, a visual stimulus, an auditory stimulus, or any other suitable stimulus. Furthermore, the stimulus can be time-locked (i.e., deployed and/or presented within a specific time window characterized by an initiation time and a termination time) and/or presented at multiple timepoints to a single user or multiple users. Additionally, provision of the stimulus/stimuli can be synchronized with user biosignal, biometric, and/or environment data substantially in real time, or upon detection of an event from user biosignal, biometric, and/or environment data. In one variation, the stimulus is deployed using a mobile device of the user, or a set of mobile devices of a group of users, such that the stimulus can be deployed at any point that a user or group of users is using the mobile device(s). In a first example, the stimulus is a command deployed on a mobile device application that tells a user to go to a specific restaurant and eat a specific menu item. In a second example, the stimulus is a music piece that is automatically deployed on a mobile device action, such that a reaction response to the music piece, captured in bioelectrical signal data collected from a user, can be analyzed. In a third example, the stimulus is a disturbing news story deployed on a mobile device, such that a reaction response to the news story can be analyzed in a manner relevant to the user's behavior change. In a fourth example, a combination of stimuli can be provided, such as a happy image rendered on a mobile device display followed by a sad music piece, such that reactions to combinations of stimuli can be later analyzed. In a fifth example with a combination of stimuli, a user or group of users can be presented with different music samples while exercising, such that responses to different types of music while exercising, captured in bioelectrical signal data, can be collected and analyzed in a manner relevant to behavior change. In a sixth example, the stimulus is automatically deployed upon detection that a user is exercising, as determined from additional biosignal, biometric, and or environment data. Thus, Step S170 allows a stimulus or a combination of scriptable stimuli to be deployed to a user or a group of users, which enables fully deployable automated experiments to be performed.

Providing a stimulus in Step S70 can also function to enable detection of evoked brain potentials that are produced in response to the provided stimulus. The evolution of these evoked potentials can indicate the degree, speed, and/or efficiency of different levels of cognitive processing following provision of the stimulus, which can allow verification that the stimulus has been received by the user, and which can further bolster analyses relevant to the user's behavior change. In one example, the stimulus can comprise an auditory stimulus, and evoked brain potentials captured in bioelectrical signal data can indicate detection of the stimulus, recognition of repetitive sequences in the stimulus, recognition of different or unexpected aspects of the stimulus, and recognition of changes in the stimulus by the user.

Step S170 can further comprise measuring the timing and/or nature of the response to the stimulus, as assessed in the collected bioelectrical signal data. In one application, the progression of evoked potentials in time and across different processing regions of the brain, in response to stimuli provided in Step S170, can provide information related to the user's ability to process the stimulus/stimuli. Furthermore, this information can be further used to provide feedback to the user (e.g., in the form of an analysis or behavior change suggestion in variations of Step S130, S140, or S160), indicating improvement, regression, or stagnation in the user's behavior. In specific examples, the feedback can indicate modifications in mental abilities corresponding to changes in lifestyle, diet, exercise, reactions to negative stimuli, progression of neurological disorders, or processing of different educational methods.

In variations of the method 100 comprising Step S170, generating an analysis in Step S130 can comprise averaging portions of bioelectrical signal datasets associated with identical or similar actions, or performing a detailed analysis of data associated with a single action using methods including independent components analysis. In either case, generating an analysis in Step S130 preferably involves usage of a data storage module (e.g., a local or remote repository) for collected bioelectrical signal data, as well as a control over stimulus provision and timing.

The method can further comprise Step S180, which recites providing at least one of the analysis and an analysis based upon the adherence metric to the user S180. Step S180 functions to provide an additional avenue to motivate a behavior change in a user, and can supplement the behavior change suggestion provided in Step S140. The analysis and/or an analysis based upon the adherence metric is preferably provided at a mobile device of the user, and can be rendered on a display of the mobile device by an application executing on the mobile device. In other variations, the analysis or analysis can be provided at any other suitable computing device (e.g., personal computer, laptop, digital assistant, tablet, etc.), and/or can be provided by another entity (e.g., health care professional, parent, teacher, supervisor) associated with the user. Providing the analysis in Step S180 can, however, be provided in any other suitable manner.

The method 100 described above can have a variety of applications, a few of which are described as exemplary applications below.

1.1 Exemplary Applications of the Method

In one specific application of the method 100, the user desires to improve his/her ability in playing an instrument. An analysis generated in a specific example of Step S130, based upon EEG signal data collected when the user is learning an "easy" piece, shows that regions of the user's brain related to stress handling show less activity in comparison to EEG signal data collected when the user is learning a more difficult piece. A behavior change suggestion in this specific application thus comprises suggestions that reduce the user's stress, as well as automatic adjustments to the user's environment (e.g., lighting, temperature, and ambient noise) that reduce stress when learning more difficult pieces. These suggestions and adjustments can thus improve the user's ability to play the instrument. A variation of this specific application can comprise providing just the melody of the music piece as a stimulus to the user, and an analysis based upon data collected from the user, in response to the stimulus, can show that the user demonstrates increased learning ability in response to auditory stimuli, which facilitates the behavior change.

In another specific application, the user is one of several employees working at a company, wherein all the employees are subject to the same working environment. Collecting bioelectrical signal data from the user in Step S110 and collecting bioelectrical signal data from the collective of employees in Step S120 can be used to generate an analysis in Step S130 that provides information related to working efficiency and the effects specific working environment aspects (e.g., internet availability, snack availability, temperature, lighting, etc.) on working efficiency. A behavior change suggestion can thus be provided to the user and/or a supervisor based upon the analysis, such that a change in the user's behavior is mediated based upon an analysis of data aggregated from the employees at the company.

In another specific application, the user is a patient suffering from post-traumatic stress disorder, and is characterized as having a negative response to loud auditory stimuli. In this specific application, the method 100 can comprise providing a loud auditory stimulus at a mobile device of the user in Step S170, collecting a bioelectrical signal dataset associated with the user's response to the stimulus in Step S110, and generating an analysis based upon the bioelectrical signal dataset in Step S130, wherein the analysis provides information related to brain regions activated by the stimulus. The behavior change suggestion can comprise suggestions to the patient to focus on aspects of the environment or memories that deactivate regions activated by the stimulus, wherein analysis of bioelectrical signal data collected from the patient while the patient focus on these aspects/memories indicates a reduction in activity in brain regions activated by the stimulus. Further collection of bioelectrical signal data from the patient, in response to the behavior change suggestion and a repeat provision of the stimulus, can be used to generate an analysis or adherence metric characterizing improvements in the patient's response to the stimulus. This specific application of the method 100 is preferably performed outside of a clinical or research environment, using a portable biosignal detector and a mobile device, such that the user's behavior change is implemented in the user's native environment and not in a contrived environment. The user can thus learn to improve his/her response to such stimuli during normal daily life.

As a person skilled in the field of biosignals will recognize from the previous detailed description and from the figures and claims, modifications and changes can be made to the embodiments, variations, examples, and specific applications of the method described above without departing from the scope of the method 100. In particular, collecting bioelectrical signal data in any of Steps S110, S120 and S150, generating an analysis in Step S130, providing a behavior change in Step S140, generating an adherence metric in Step S160, and/or providing a stimulus in Step S170 can be performed in any suitable order and in any suitable number of iterations, as noted in the variations and exemplary applications described above.

2. System

Figure 6:
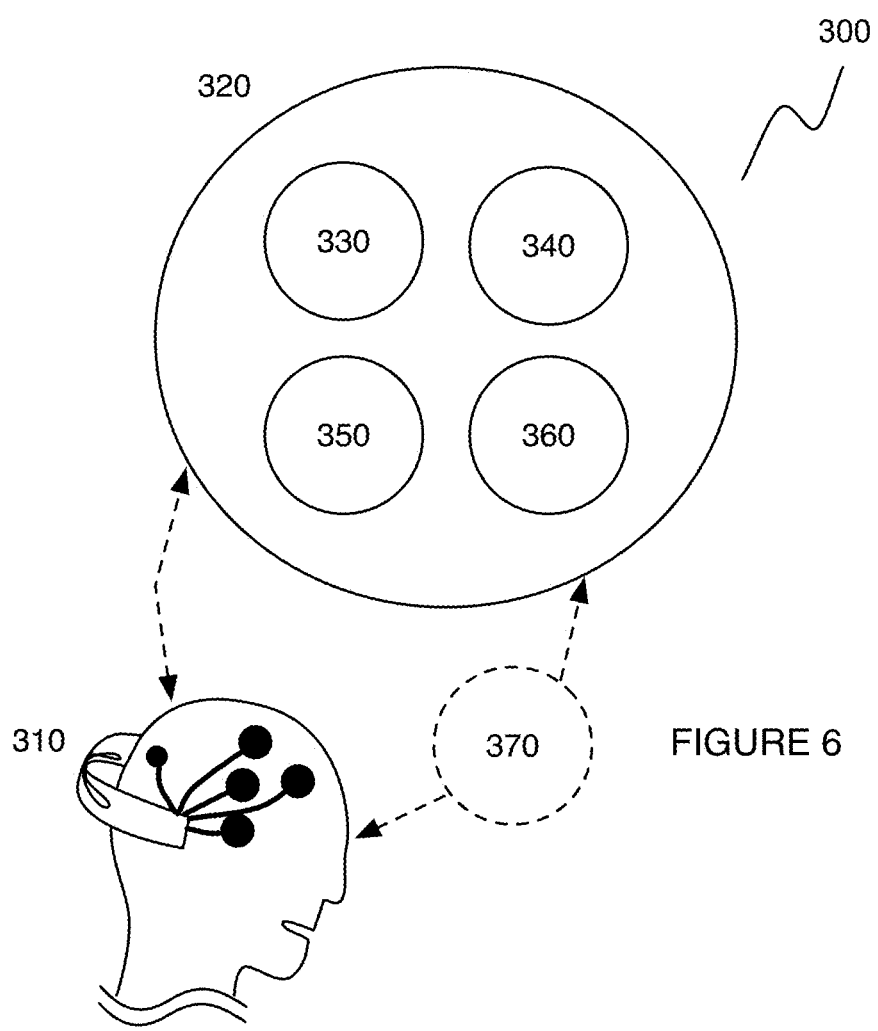
FIG. 6 is a schematic of an embodiment of a system for instructing a behavior change in a user.

As shown in FIG. 6, an embodiment of a system 300 for providing and aggregating bioelectrical signal data comprises a biosignal detector 310 and a processor 320 comprising a receiver 330, an analyzer 340, a transmitter 350, and a stimulus transmission module 360. The system 300 can further comprise a data storage module 370 that receives data relevant to a user's behavior change. The system 300 functions to facilitate collection of bioelectrical signal data while a user engages in a particular action associated with the user's behavior change, to generate an analysis based upon bioelectrical signal and/or other data collected from the user, and to provide a behavior change suggestion to the user based upon the analysis. The system 300 preferably enables a variation of the method 100 described above, but can alternatively facilitate performance of any suitable method involving collection and analysis of bioelectrical signal data to promote a behavior change in a user.

The biosignal detector 310 functions to collect bioelectrical signal data from a user. The biosignal detector 310 preferably comprises a bioelectrical signal sensor system, wherein the sensor system comprises a plurality of sensors, each sensor providing at least one channel for bioelectrical signal capture. The plurality of sensors can be placed at specific locations on the user, in order to capture bioelectrical signal data from multiple regions of the user. Furthermore, the sensor locations can be adjustable, such that the biosignal detector 310 is tailorable to each user's unique anatomy. Alternatively, the sensor system can comprise a single bioelectrical signal sensor configured to capture signals from a single region of the user. In one example, the biosignal detector can be a personal EEG device, such as the Emotiv EPOC neuroheadset, which is shown in FIG. 2. EEG devices are taught in the U.S. Patent Publication Nos. 2007/0066914 (Emotiv) and 2007/0173733 (Emotiv), which are also incorporated in their entirety herein by this reference.

The biosignal detector 310 can also comprise or be coupled to additional sensor systems configured to capture data related to other biological processes of the user and/or the environment of the user. As such, the biosignal detector 310 can comprise optical sensors to receive visual information about the user's environment, GPS elements to receive location information relevant to the user, audio sensors to receive audio information about the user's environment, temperature sensors, sensors to detect MEG impedance or galvanic skin response (GSR), sensors to measure respiratory rate, and/or any other suitable sensor. Furthermore, the system can comprise multiple biosignal detectors, each paired with a given user, such that bioelectrical signal data can be simultaneously collected from more than one user.

The processor 320 comprises a receiver 330, an analyzer 340, a transmitter 350, and a stimulus transmission module 360, and functions to receive and process bioelectrical signal data, biosignal data, and/or any other suitable data from the user or group of users. As such, the processor 320 can comprise a remote server configured to perform the functions of at least one of the receiver 330, the analyzer 340, the transmitter 350, and the stimulus transmission module 360. In this embodiment, the remote server can execute analysis tools to facilitate processing, analysis, storage, and/or transmission of data; however, the processor 320 can alternatively comprise any other suitable element or combinations of elements.

The receiver 330 functions to receive bioelectrical signal datasets from a single user or multiple users. The receiver 330 preferably comprises a wireless connection to a biosignal detector (or other suitable element for data transfer); however, the receiver 330 can alternatively comprise a wired connection. In wireless variations, the receiver 330 can implement wireless communications, including Bluetooth, 3G, 4G, radio, or Wi-Fi communication. In these variations, data and/or signals are preferably encrypted before being received by the receiver 330. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

The analyzer 340 functions to generate an analysis of collected bioelectrical signal data and any other biosignal, biometric, and/or environment data from the user(s), in order to provide the basis for a behavior change suggestion. In some variations, the analyzer 340 can further function to generate the behavior change suggestion, an adherence metric, and/or an analysis based upon the adherence metric to a user. The analyzer 340 preferably implements signal analysis techniques (e.g., independent component analysis) and data mining algorithms; however, the analyzer 340 can additionally or alternatively implement any suitable methods or algorithms for processing and/or comparing bioelectrical signal datasets. In a first variation, the analyzer 340 is configured to generate an analysis based upon multiple bioelectrical signal datasets collected from a single user. In a second variation, the analyzer 340 is configured to generate an analysis based upon bioelectrical signal datasets from multiple users.

The transmitter 350 functions to transmit at least one of a generated analysis and a behavior change suggestion to the user. As such, the transmitter is preferably configured to communicate with a device of the user in order to electronically provide the analysis and/or behavior change suggestion at a user-device interface. In other variations, the transmitter can provide the analysis and/or behavior change suggestion to an intermediate entity (e.g., storage module, third party) that further conveys the analysis/behavior change suggestion to the user. The transmitter 350 can alternatively comprise any other suitable element(s) configured to transmit information to a user.

The stimulus transmission module 360 functions to facilitate provision of a stimulus or combination of stimuli to a user, in order to prompt an action by the user related to the user's behavior change. As such, the stimulus transmission module 360 can comprise an alert system that provides a notification to the user, a module that gives a command to the user instructing the user to perform an action, a haptics system configured to provide haptic stimulus, a display configured to render a visual stimulus, an audio system configured to provide an audio stimulus, and/or any other suitable stimulus transmission system. Preferably, the stimulus transmission module comprises a controller that controls delivery of the stimulus/stimuli, with regard to timing, frequency, and/or duration. In one variation, at least a portion of the stimulus transmission module 360 is implemented on a mobile device of the user, or a set of mobile devices of a group of users, such that a given stimulus or combination of stimuli can be deployed whenever a user or group of users is using the mobile device(s). The system 300 can, however, comprise any other suitable stimulus transmission elements to provide a stimulus to one or more users.

The system 300 can further comprise a data storage module 370, which functions to receive and store data associated with the user's behavior change. Preferably, bioelectrical signal data and other enriching data is transmitted to and maintained by the data storage module 370. Furthermore, the data storage module 370 is preferably remote from the biosignal detector 310. As such, bioelectrical signal data of the first user and multiple other users are preferably collected over time and stored by the data storage module 370 at a remote location. The data storage module also preferably maintains aggregate bioelectrical signal data including anonymized (e.g., stripped of personal or identifying information) data of the first user and other users, wherein the aggregate data is preferably assembled into buckets defining a particular action or group of similar actions performed by users during recordation of bioelectrical signals. In some variations, the data storage module 370 can be a remote server configured to host or communicate with an application programming interface (API), wherein the API allows accessing and manipulation of data stored in the data storage module 370. In one example, the biosignal detector 310 can be Internet-capable and transmit data directly to the data storage module 370, or the biosignal detector 310 can communicate via a wireless or wired connection with a local electronic device, such as a smartphone or tablet, that transmits the data to the data storage module 370. In the example, the data storage module can thus be hosted by a remote server in a manner compliant with privacy laws (e.g., HIPAA compliance) or can be hosted in any suitable cloud storage module. Alternatively, bioelectrical signal data and additional enriching data can be maintained by a data storage module 370 that operates, at least in part, on an electronic device that is local to the user and configured to communicate with the biosignal detector 310. In any of the foregoing variations, the bioelectrical signal data and enriching data is preferably accessible by the user, from the data storage module 370, to view, augment, or update any portion of the data. Data can be transmitted to the data storage module 370 substantially in real time, such as during recordation of the signal, or once the data collection is completed, verified, or released by the user.

The method 100 and system 300 of the preferred embodiment and variations thereof can be embodied and/or implemented at least in part as a machine configured to receive a computer-readable medium storing computer-readable instructions. The instructions are preferably executed by computer-executable components preferably integrated with the system 300 and one or more portions of the processor 320 and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals will recognize from the previous detailed description and from the figures and claims, modifications and changes can be made to the preferred embodiments of the invention without departing from the scope of this invention defined in the following claims.

We claim:

1. A method for facilitating user behavior change with a biosignal neuroheadset, the method comprising:
   providing a first stimulus to a user, wherein the first stimulus is configured to prompt a first action;
   with the biosignal neuroheadset, collecting a bioelectrical signal dataset associated with the user performing the first action;
   with a motion sensor, collecting a motion dataset associated with the user performing the first action;
   with a processor of a remote server:
      identifying the first action based on the motion dataset;
      generating an analysis of the bioelectrical signal dataset based on the first action;
      receiving a location dataset collected at a location sensor in association with the user performing the first action; and
      determining a behavior change suggestion based on the analysis and the location dataset;
   transmitting the behavior change suggestion to a computing device and electronically providing the behavior change suggestion to the user via a user-device interface; and
   providing a second stimulus associated with the behavior change suggestion.

2. The method of claim 1, wherein the behavior change suggestion facilitates adjustment of an aspect of the user's environment, wherein the aspect comprises at least one of lighting, temperature, and sound.

3. The method of claim 1, wherein the first stimulus comprises first content, wherein generating the analysis of the bioelectrical signal dataset comprises generating a brain activity analysis associated with the user receiving the first content, and wherein determining the behavior change suggestion comprises determining the behavior change suggestion based on the brain activity analysis and the location dataset.

4. The method of claim 3, wherein the second stimulus comprises an advertisement, wherein the behavior change suggestion facilitates adjustment of at least one of timing, frequency and duration associated with the advertisement.

5. The method of claim 1, wherein the first stimulus comprises an audio stimulus, and wherein the second stimulus comprises a modified audio stimulus based on the behavior change suggestion.

6. The method of claim 1, wherein the biosignal neuroheadset comprises the motion sensor, and wherein the computing device comprises the location sensor.

7. The method of claim 1, wherein generating the analysis of the bioelectrical signal dataset comprises generating, with the processor of the remote server, the analysis based on anonymized bioelectrical signal data associated with a set of supplemental users and the first action.

8. A method for facilitating user behavior change with a biosignal neuroheadset, the method comprising:
   providing a first stimulus to a user, wherein the first stimulus is configured to prompt a first action;
   with the biosignal neuroheadset, collecting a bioelectrical signal dataset associated with the user performing the first action;
   with a motion sensor, collecting a motion dataset associated with the user performing the first action;
   with a processor of a remote server:
      identifying the first action based on the motion dataset;
      generating an analysis of the bioelectrical signal dataset based on the first action; and determining a behavior change suggestion based on the analysis;

transmitting the behavior change suggestion to a computing device; and automatically adjusting an aspect of the user's environment based on the behavior change suggestion, wherein the aspect comprises at least one of lighting, temperature and sound.

\* \* \* \* \*